United States Patent [19]

Oka et al.

[11] 4,148,897

[45] Apr. 10, 1979

[54] 1,2-DIHYDRONAPHTHALENE DERIVATIVES AND PHARMACEUTICAL COMPOSITION

[75] Inventors: Yoshikazu Oka, Kobe; Katsumi Itoh, Takatsuki; Akio Miyake, Hirakata; Minoru Hirata, Takatsuki, all of Japan

[73] Assignee: Takeda Chemical Industries, Ltd., Osaka, Japan

[21] Appl. No.: 789,278

[22] Filed: Apr. 20, 1977

[30] Foreign Application Priority Data

Apr. 29, 1976 [JP] Japan .................................. 51/48905

[51] Int. Cl.² ................... A61K 31/495; C07D 295/08
[52] U.S. Cl. ................... 424/250; 424/248.4; 424/248.57; 544/173; 544/174; 544/378; 544/391; 544/396; 544/398; 544/401; 544/402; 544/403
[58] Field of Search ................... 260/268 BC, 268 TR; 424/250; 544/377, 391, 398, 401, 402, 403, 396

[56] References Cited

U.S. PATENT DOCUMENTS

| 3,845,058 | 10/1974 | Lembo et al. ................. 260/268 BC |
| 3,886,168 | 5/1975 | Himmele et al. ............. 260/268 BC |
| 3,919,230 | 11/1975 | Hill et al. ..................... 260/268 BC |
| 4,022,791 | 5/1977 | Welch ............................ 544/403 |
| 4,035,498 | 7/1977 | Mauvernay et al. .......... 260/268 BC |

*Primary Examiner*—Paul M. Coughlan, Jr.
*Attorney, Agent, or Firm*—Wenderoth, Lind & Ponack

[57] ABSTRACT

Novel 1,2-dihydronaphthalene derivatives of the formula

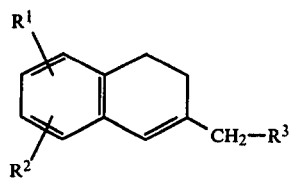

wherein $R^1$ and $R^2$, independently of each other, are hydrogen, nitro, amino, halogen, or hydroxyl which may be protected, and $R^3$ is a piperazinyl or morpholino group which may be substituted by lower alkyl, aralkyl, carboxylic acid-derived acyl, lower alkoxycarbonyl-lower alkyl or cycloaminocarbonyl-lower alkyl, and its salts have excellent pharmacological activities such as vasodilator and cerebral blood flow increasing activities.

12 Claims, No Drawings

1,2-DIHYDRONAPHTHALENE DERIVATIVES AND PHARMACEUTICAL COMPOSITION

The present invention relates to novel and useful 1,2-dihydronaphthalene derivatives.

1,2-Dihydronaphthalene derivatives substituted with cyclic amino-methyl groups at the 3-position have been unknown with an exception of 3-piperidinomethyl-1,2-dihydronaphthalene described in "Archiv der Pharmazie" 275, 54 et seq. (1937). The literature, however, does not refer to any pharmacological activity of the said compound.

The present inventors have succeeded in producing novel 1,2-dihydronaphthalene derivatives of the formula

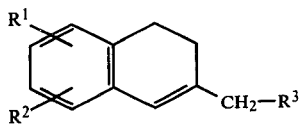

wherein $R^1$ and $R^2$, independently of each other, are hydrogen, nitro, amino, halogen, or hydroxyl which may be protected, and $R^3$ is a piperazinyl or morpholino group which may be substituted by lower alkyl, aralkyl, carboxylic acid-derived acyl, lower alkoxycarbonyl-lower alkyl or cycloaminocarbonyl-lower alkyl, and its salts, and further studies on these compounds have unexpectedly revealed that they exhibit excellent pharmacological activities such as vasodilator and cerebral blood flow increasing activities and are of value, for example, as drugs for the management of impaired cerebral circulation and as peripheral vasodilators.

Thus, the principal object of the present invention is to provide the novel 1,2-dihydronaphthalene derivatives (I) and their physiologically acceptable salts which have the excellent pharmacological activities, and another object is to provide a pharmaceutical composition comprising one or more of these compounds. A further object is to provide an industrially feasible method for producing these compounds. Other objects will be made clear from the description and claims presented hereinafter.

Referring to the formula (I), $R^1$ and $R^2$, independently of each other, are hydrogen, nitro, amino, halogen, or hydroxyl which may be protected. Said hydroxyl, when it is protected, may be, for example, one of lower alkoxys and aralkyloxys, and $R^1$ and $R^2$ may, taken together, form an alkylenedioxy. Such lower alkoxys may be straight-chain or branched, thus including methoxy, ethoxy, propoxy, butoxy, isopropoxy and amyloxy, with alkoxys containing up to 5 carbon atoms being particularly advantageous. Said aralkyloxys are such that their alkyl moieties may be straight-chain or branched, including benzyloxy, phenethyloxy, α-methylphenethyloxy, and naphthylmethyloxy, with aralkyloxys containing a total of about 7 to 12 carbon atoms being particularly advantageous. Said lower alkylenedioxys include methylenedioxy, ethylenedioxy and trimethylenedioxy, for instance, with alkylenedioxys containing up to 3 carbon atoms being preferred. The halogen $R^1$ may be any of fluorine, chlorine, bromine and iodine. Such group $R^1$, $R^2$ may be situated at any of the 5-, 6-, 7- and 8-positions on the 1,2-dihydronaphthalene ring.

In the formula (I), $R^3$ stands for a piperazinyl or morpholino group which may be substituted by lower alkyl, aralkyl, carboxylic acid-derived acyl, lower alkoxycarbonyl-lower alkyl or cycloaminocarbonyl-lower alkyl. The lower alkyl may be straight-chain or branched, being thus exemplified by methyl, ethyl, isopropyl, butyl and amyl. Particularly preferred are lower alkyls containing up to 5 carbon atoms. The aralkyl may be those consisting of straight-chain or branched lower alkyls substituted by one or two aryl groups, such as benzyl, α-methylbenzyl, benzhydryl, phenethyl, α-methylphenethyl and naphthylmethyl, with straight-chain lower alkyls of 1 to 3 carbon atoms substituted in ω-position by one or two phenyls being particularly advantageous. The carboxylic acid-derived acyl groups may be those derived from any of aliphatic carboxylic acids, aromatic carboxylic acids, heterocyclic carboxylic acids, including acetyl, propionyl, butyryl, isobutyryl, benzoyl, toluoyl, phenylacetyl, furoyl, nicotinoyl and 3,4,5-trimethoxybenzoyl, to name but a few, with those containing a total of up to 10 carbon atoms being particularly advantageous. As the lower alkoxycarbonyl-lower alkyls may be mentioned ethoxycarbonylmethyl, propoxycarbonylmethyl, butoxycarbonylmethyl, isopropoxycarbonylmethyl, β-methoxycarbonylethyl and γ-methoxycarbonylpropyl, with lower alkoxycarbonyl-lower alkyls containing a total of up to 6 carbon atoms being particularly desirable. The cycloamino moiety of the cycloaminocarbonyl-lower alkyl group is preferably pyrrolidinyl, with the lower alkyl moiety preferably containing about 1 to 3 carbon atoms. When $R^3$ is piperazinyl, such a substituent is advantageously situated in its $N^4$-position. Where $R^3$ is morpholino, preferred substituents are lower alkyls substituted at the 2- or/and 3-positions thereof. The preferred examples of such substituted piperazinyl and morpholino groups include 4-methyl-1-piperazinyl, 4-benzhydryl-1-piperazinyl, 4-acetyl-1-piperazinyl, 4-butyryl-1-piperazinyl, 4-nicotinoyl-1-piperazinyl, 4-ethoxycarbonylmethyl-1-piperazinyl, 4-pyrrolidinylcarbonylmethyl-1-piperazinyl, 2-methylmorpholino and 2,3-dimethylmorpholino. Among them, more advantageous is the piperazinyl group substituted at the $N^4$-position by the aralkyl or the carboxylic acid-derived acyl, especially by the straight-chain lower alkyl of 1 to 3 carbon atoms substituted in at the ω-position by one or two phenyls.

The 1,2-dihydronaphthalene derivatives of the formula (I) may be produced in good yield by, for example, subjecting a compound of the formula

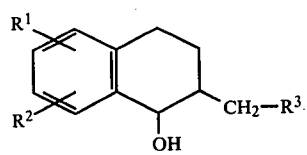

wherein $R^1$, $R^2$ and $R^3$ have the same meanings as defined above to dehydration reaction. This dehydration reaction is generally accomplished by placing a compound (II) under conditions of dehydration in an appropriate solvent. While the conditions of dehydration may be established by any technique per se known to one skilled in organic chemistry, preferred techniques include the following. Thus, by way of example, one may conduct the reaction by the presence of a mineral acid, e.g. hydrochloric acid, sulfuric acid or nitric acid; a Lewis acid, e.g. aluminum chloride, zinc chloride and boron trifluoride; a phosphoric acid compound, e.g.

phosphoric acid and polyphosphoric acid; an organic acid, e.g. acetic acid, propionic acid, benzenesulfonic acid, p-toluenesulfonic acid and methanesulfonic acid; or an acid salt such as sodium hydrogen sulfate and potassium hydrogen sulfate. An alternative procedure comprises reacting the starting compound with a dehydrating agent such as an acid anhydride, e.g. acetic anhydride, propionic anhydride, phthalic anhydride or phosphoric anhydride, or an acid halide, e.g. phosphorus oxychloride or thionyl chloride. The solvent may be any solvent that will not interfere with the reaction. Thus, for example, water, methanol, ethanol, isopropanol, acetone, methyl ethyl ketone, ethyl acetate, chloroform, diethyl ether, benzene, toluene, dioxane, tetrahydrofuran, dimethylsulfoxide, dimethylformamide, pyridine and triethylamine as well as mixtures of such solvents may be mentioned. Depending upon the types of dehydrating agent, solvent and compound (II) employed, among other conditions, the reaction may normally be accomplished successfully at temperatures within the range of about 0° C. to about 200° C. In conducting this dehydration reaction, the starting compound (II) may be employed in the form of free base or as an acid addition salt similar to that which will hereinafter be mentioned in connection with the compounds (I).

The 1,2-dihydronaphthalene derivatives (I) thus produced may be isolated in the form of free base or as a salt, by conventional separation and purification procedures such as extraction, concentration, neutralization, filtration, recrystallization, distillation and column chromatography. By procedures known per se, the free base may be converted to physiologically acceptable acid addition salts such as inorganic acid salts (e.g. hydrochloride, hydrobromide, sulfate, nitrate) or organic acid salts (e.g. maleate, fumarate, malate, tartrate, toluenesulfonate, naphthalenesulfonate, methanesulfonate).

The novel 1,2-dihydronaphthalene derivatives of the formula (I) and salts thereof according to this invention have excellent vasodiator and cerebral blood flow increasing activities as well as other desirable pharmacological activities such as antihistaminic activity, and these properties plus their low toxicity make these compounds valuable as drugs, for example, for the treatment of circulatory diseases, such as drugs for the management of impaired cerebral circulation, and peripheral vasodilators in mammalian animals (human beings; domesticated animals such as dogs and cats; laboratory animals such as rats and mice). Where the compound of this invention is employed as such a drug, it may be administered orally or parenterally either as it is or as formulated with suitable pharmaceutically acceptable carriers, excipients or diluents in such varied dosage forms as powders, granules, tablets, capsules and injections. The dosage may be chosen depending on the disease to be managed and the route of administration. For instance, when the present compounds are administered to adult humans as a drug for the treatment of the disturbance of cerebral circulation, e.g. for the treatment of cerelral apoplexy (cerebral haemorrhage, cerebral thrombosis and cerebral embolism), cerebral arteriosclerosis, hypertensive cerebral circulatory insufficiency, sequelae of head injury, etc., advantageous dose levels are of about 10 to 500 mg., especially about 20 to 200 mg. daily by the oral route, or about 1 to 50 mg., especially about 2 to 20 mg. daily by the intravenous route.

The starting compound (II) for the present invention may be easily produced, for example by the method described in "Archiv der Pharmazie" 275, 54 et seq. (1937) or a method analogous thereto, by way of the route of synthesis shown below in formulas:

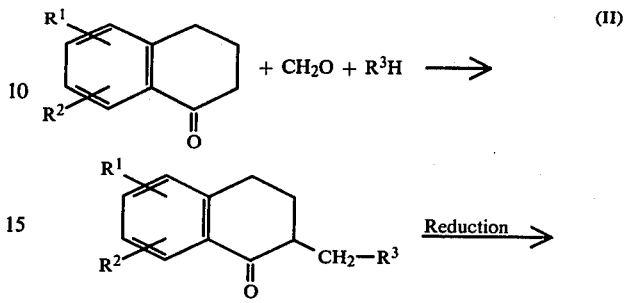

In the formulas, $R^1$, $R^2$ and $R^3$ have the same meanings as defined hereinbefore.

The following Examples and Experimental are further illustrative of this invention. It should, of course, be understood that the scope of the invention is by no means limited by and to these examples.

Throughout the foregoing description as well as in the following Examples and Experimental, "g.", "mg.", "ml." and "° C." respectively refer to "gram(s)", "milligram(s)", "milliliter(s)" and "degree(s) centigrade".

EXAMPLE 1

In 50 ml. of ethanol is dissolved a mixture of 3.5 g. of 5,6-dimethoxy-3,4-dihydro-1(2H)-naphthalenone, 7 g. of 1-benzhydrylpiperazine hydrochloride and 3.5 g. of 37% aqueous formalin and the solution is allowed to stand at room temperature overnight. To the reaction mixture is added 500 ml. of water and, after shaking with 100 ml. of diethyl ether, the water layer is neutralized with sodium hydrogen carbonate and extracted with chloroform. The extract is dried over anhydrous sodium sulfate and distilled under reduced pressure to remove the solvent. The residue is crystallized by the addition of methanol. By the above procedure is obtained 3.5 g. of 2-(4-benzhydryl-1-piperazinylmethyl)-5,6-dimethoxy-3,4-dihydro-1(2H)-naphthalenone as colorless crystals melting at 134°–136° C.

Elemental analysis, for $C_{30}H_{34}O_3H_2$—Calculated: C, 76.56; H, 7.28; N, 5.95. Found: C, 76.85; H, 7.07; N, 5.80.

In a mixture of 20 ml. of chloroform and 100 ml. of methanol is dissolved 3.5 g. of 2-(4-benzhydryl-1-piperazinylmethyl)-5,6-dimethoxy-3,4-dihydro-1(2H)-naphthalenone. Following the addition of 2.5 g. of sodium borohydride, the solution is stirred at room temperature for 30 minutes. The reaction mixture is then diluted with 500 ml. of water and extracted with chloroform. The extract is dried over anhydrous sodium sulfate and distilled under reduced pressure to remove the solvent. The residue is purified by chromatography on a column of silica gel (acetone-benzene=1:9). To the resultant oil is added a methanolic solution of fumaric acid, followed by the addition of diethyl ether. By the above procedure is obtained 1.4 g. of 2-(4-benzhydryl-1-piperazinylmethyl)-5,6-dimethoxy-1,2,3,4-tetrahydro-1-naphthalenol hydrogen fumarate as colorless prisms melting at 195°–200° C. (decomposition).

Elemental analysis, for $C_{30}H_{36}O_3N_2 \cdot C_4H_4O_4$ — Calculated: C, 69.37; H, 6.85; N, 4.76. Found: C, 69.49; H, 6.86; N, 4.82.

In a mixture of 10 ml. of ethanolic hydrochloric acid and 50 ml. of methanol is dissolved 0.8 g. of 2-(4-benzhydryl-1-piperazinylmethyl)-5,6-dimethoxy-1,2,3,4-tetrahydro-1-naphthalenol hydrogen fumarate and the solution is heated at 80°–90° C. for 30 minutes. The reaction mixture is concentrated and ethanol is added to the residue, followed by cooling. By the above procedure is obtained 0.65 g. of 3-(4-benzhydryl-1-piperazinylmethyl)-7,8-dimethoxy-1,2-dihydronaphthalene hydrochloride as colorless needles melting at 225°–240° C. (decomposition).

Elemental analysis, for $C_{30}H_{34}O_2N_2 \cdot 2HCl$ — Calculated: C, 68.30; H, 6.88; N, 5.31. Found: C, 68.16; H, 6.94; N, 5.35.

EXAMPLE 2

In 100 ml. of ethanol is dissolved a mixture of 1 g. of 6-methoxy-5-nitro-3,4-dihydro-1(2H)-naphthalenone and 3 g. of morpholine hydrochloride and the mixed solution is reacted at 80° C. for 10 hours. The reaction mixture is cooled and, following addition of 500 ml. of water, it is shaken with 100 ml. of diethyl ether. The water layer is neutralized with sodium hydrogen carbonate and extracted with chloroform. The extract is dried and distilled under reduced pressure to remove the solvent. By the above procedure is obtained 6-methoxy-2-morpholinomethyl-5-nitro-3,4-dihydro-1(2H)-naphthalenone as an oily product. This product is dissolved in 50 ml. of methanol and, after addition of 1 g. of sodium borohydride, the solution is stirred at room temperature for 30 minutes. To this reaction mixture is added 500 ml. of water and the mixture is extracted with chloroform. The extract is dried and distilled under reduced pressure to remove the solvent. The above procedure provides an oil of 6-methoxy-2-morpholinomethyl-5-nitro-1,2,3,4-tetrahydro-1-naphthalenol. This product is dissolved in 20 ml. of ethanolic hydrochloric acid and the solution is heated at 80° C. for 1 hour. Following the addition of 50 ml. of ethyl acetate, the solution is cooled, whereupon 0.35 g. of 7-methoxy-3-morpholinomethyl-8-nitro-1,2-dihydronaphthalene hydrochloride is obtained as pale-yellow prisms melting at 200°–270° C. (gradually decomposed).

Elemental analysis, for $C_{16}H_{20}O_4N_2 \cdot HCl \cdot \frac{1}{2}H_2O$ — Calculated: C, 54.93; H, 6.34; N, 8.01. Found: C, 55.16; H, 6.31; N, 7.89.

EXAMPLE 3

In 100 ml. of ethanol is dissolved a mixture of 5 g. of 6,7-dimethoxy-3,4-dihydro-1(2H)-naphthalenone, 8 g. of 1-benzhydrylpiperazine hydrochloride and 10 g. of 37% aqueous formalin and the solution is allowed to stand at room temperature overnight, after which time it is heated at 80° C. for 7 hours. To the reaction mixture is added 500 ml. of water and, after shaking with 100 ml. of diethyl ether, the water layer is neutralized with sodium hydrogen carbonate and extracted with chloroform. The extract is dried and distilled under reduced pressure. To the oily residue is added methanol, whereupon 5 g. of 2-(4-benzhydryl-1-piperazinylmethyl)-6,7-dimethoxy-3,4-dihydro-1(2H)-naphthalenone is obtained as colorless crystals melting at 142°–144° C.

Elemental analysis, for $C_{30}H_{34}O_3N_2$ — Calculated: C, 76.56; H, 7.28; N, 5.95. Found: C, 76.62; H, 7.41; N, 6.11.

In a mixture of 50 ml. of chloroform and 50 ml. of methanol is dissolved 5 g. of 2-(4-benzhydryl-1-piperazinylmethyl)-6,7-dimethoxy-3,4-dihydro-1(2H)-naphthalenone, followed by addition of 5 g. of sodium borohydride. The mixture is stirred at room temperature for 30 minutes. Following addition of 500 ml. of water, the reaction mixture is extracted with chloroform, dried over anhydrous sodium sulfate and distilled under reduced pressure to remove the solvent. The oily residue is purified by chromatography on a column of silica gel (acetone-benzene=1:9), followed by the addition of an ethanolic solution of fumaric acid, and diethyl ether. By the above procedure is obtained 2.5 g. of 2-(4-benzhydryl-1-piperazinylmethyl)-6,7-dimethoxy-1,2,3,4-tetrahydro-1-naphthalenol hydrogen fumarate as colorless crystals melting at 164°–167° C.

Elemental analysis, for $C_{30}H_{36}O_3N_2 \cdot C_4H_4O_4$ — Calculated: C, 69.37; H, 6.85; N, 4.76. Found: C, 69.67; H, 6.93; N, 5.01.

In 50 ml. of ethanolic hydrochloric acid is dissolved 1.3 g. of 2-(4-benzhydryl-1-piperazinylmethyl)-6,7-dimethoxy-1,2,3,4-tetrahydro-1-naphthalenol hydrogen fumarate and the solution is heated at 80° C. for 2 hours. The reaction mixture is then concentrated to one-half of its original volume and cooled. By the above procedure is obtained 1.1 g. of 3-(4-benzhydryl-1-piperazinylmethyl)-6,7-dimethoxy-1,2-dihydronaphthalene hydrochloride as colorless prisms melting at 230°–243° C. (decomposition).

Elemental analysis, for $C_{30}H_{34}O_2N_2 \cdot 2HCl$ — Calculated: C, 68.30; H, 6.88; N, 5.31. Found: C, 68.15; H, 6.85; N, 5.10.

EXAMPLE 4

In 100 ml. of ethanol is dissolved a mixture of 10 g. of 3,4-dihydro-1(2H)-naphthalenone, 22 g. of 1-benzhydrylpiperazine hydrochloride and 10 g. of 37% aqueous formalin and the mixed solution is stirred at room temperature for 3 hours and, then, heated at 80° C. for another 3 hours. To this reaction mixture is added 500 ml. of water and, after shaking with 100 ml. of diethyl ether, the water layer is neutralized with sodium hydrogen carbonate and extracted with chloroform. The extract is dried over anhydrous sodium sulfate and distilled under reduced pressure to remove the solvent. By the above procedure is obtained an oil of 2-(4-benzhydryl-1-piperazinylmethyl)-3,4-dihydro-1(2H)-naphthalenone. This product is dissolved in a mixture of 50 ml. of chloroform and 100 ml. of methanol. After addition of 5 g. of sodium borohydride, the mixture is stirred at room temperature for 30 minutes. Following addition of 500 ml. of water, the reaction mixture is extracted with chloroform and the extract is dried. The solvent is distilled off under reduced pressure and the residue is purified by chromatography on a column of silica gel (acetone-benzene=1:9). By the above procedure is obtained 4.3 g. of 2-(4-benzhydryl-1-piperazinylmethyl)-1,2,3,4-tetrahydro-1-naphthalenol as colorless prisms melting at 179°–181° C.

Elemental analysis, for $C_{28}H_{32}ON_2$ — Calculated: C, 81.51; H, 7.82; N, 6.79. Found: C, 81.70; H, 7.79; N, 6.63.

To 2.3 g of 2-(4-benzhydryl-1-piperazinylmethyl)-1,2,3,4-tetrahydro-1-naphthalenol is added 70 ml. of ethanolic hydrochloric acid and the mixture is heated at 80° C. for 3 hours, after which time it is concentrated and cooled. By the above procedure is obtained 1.7 g. of 3-(4-benzhydryl-1-piperazinylmethyl)-1,2-dihydronaphthalene hydrochloride as colorless needles melting at 225°–230° C. (decomposition).

Elemental analysis, for $C_{28}H_{30}H_2 \cdot 2HCl$ — Calculated: C, 71.94; H, 6.90; N, 5.99. Found: C, 72.03; H, 6.56; N 5.95.
EXAMPLES 5 to 29
The 1,2-dihydronaphthalene derivatives listed in Table 1 are produced by subjecting the corresponding tetralol compounds to dehydration reaction in a similar manner to those described in Examples 1 to 4.
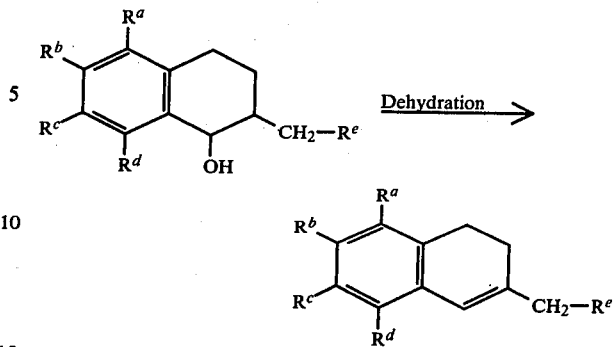

Table 1

| Example No. | $R^a$ | $R^b$ | $R^c$ | $R^d$ | $R^e$ | Salt | Melting point (°C.) (decomposition) | Molecular formula | Elemental analysis (%)* C H N |
|---|---|---|---|---|---|---|---|---|---|
| 5 | —H | —H | —H | —H | morpholino | HCl | 240–242 | $C_{15}H_{19}ON \cdot HCl$ | 67.78 7.59 5.27 / 67.59 7.58 5.49 |
| 6 | —H | —H | —H | —H | 4-benzylpiperazino | 2HCl | 240–246 | $C_{22}H_{26}N_2 \cdot 2HCl$ | 67.51 7.21 7.16 / 67.62 7.22 7.11 |
| 7 | —H | —OCH₃ | —H | —H | morpholino | HCl | 219–221 | $C_{16}H_{21}O_2N \cdot HCl$ | 64.96 7.50 4.74 / 64.80 7.55 4.89 |
| 8 | —OCH₃ | —OCH₃ | —H | —H | morpholino | HCl | 220–225 | $C_{17}H_{23}O_3N \cdot HCl$ | 62.66 7.42 4.30 / 62.78 7.42 4.12 |
| 9 | —OCH₃ | —OCH₃ | —H | —H | 4-methylpiperazino | 2HCl | 238–256 | $C_{18}H_{26}O_2N_2 \cdot 2HCl$ | 57.60 7.52 7.42 / 57.33 7.60 7.51 |
| 10 | —NO₂ | —OCH₃ | —H | —H | 4-benzhydrylpiperazino | 2HCl | 240–245 | $C_{29}H_{31}O_3N_3 \cdot 2HCl$ | 64.20 6.13 7.75 / 64.10 6.13 7.82 |
| 11 | —H | —OCH₃ | —OCH₃ | —H | morpholino | HCl | 225–226 | $C_{17}H_{23}O_3N \cdot HCl$ | 62.66 7.42 4.30 / 62.56 7.32 4.28 |
| 12 | —H | —OCH₃ | —NO₂ | —H | morpholino | HCl | 230–240 | $C_{16}H_{20}O_4N_2 \cdot HCl$ | 56.38 6.21 8.22 / 56.04 6.21 7.93 |
| 13 | —OCH₃ | —H | —H | —OCH₃ | morpholino | HCl | 205–215 | $C_{17}H_{23}O_3N \cdot HCl$ | 62.66 7.42 4.30 / 62.75 7.33 4.06 |

Table 1-continued

| Example No. | $R^a$ | $R^b$ | $R^c$ | $R^d$ | $R^e$ | Salt | Melting point (°C.) (decomposition) | Molecular formula | Elemental analysis (%)* C H N |
|---|---|---|---|---|---|---|---|---|---|
| 14 | —OCH₃ | —H | —H | —OCH₃ | N-piperidine-CH(C₆H₅)₂ | — | 112–114 | C₃₀H₃₄O₂N₂·H₂O | 76.24 7.68 5.93 / 75.95 7.32 5.86 |
| 15 | —H | —OCH₃ | —H | —H | 2-CH₃-morpholine | HCl | 215–220 | C₁₇H₂₃O₂N·HCl | 65.90 7.81 4.52 / 65.72 7.90 4.44 |
| 16 | —H | —OCH₃ | —H | —H | N-(CH₂)₃CH₃-piperazine | 2HCl | 222 | C₂₀H₃₂ON₂·2HCl | 61.68 8.80 7.19 / 61.74 8.50 7.22 |
| 17 | —H | —OCH₂C₆H₅ | —H | —H | morpholine | HCl | 211–218 | C₂₂H₂₅O₂N·HCl | 71.05 7.05 3.77 / 70.90 7.08 3.68 |
| 18 | —H | —OH | —H | —H | morpholine | HCl | 211–214 | C₁₅H₁₉O₂N·HCl | 63.93 7.15 4.97 / 63.93 7.20 4.93 |
| 19 | —NH₂ | —OCH₃ | —H | —H | morpholine | 2HCl | 170–175 | C₁₆H₂₂O₂N₂·2HCl·EtOH·H₂O | 52.55 7.84 6.81 / 52.77 7.62 6.88 |
| 20 | —OC₄H₉ | —OCH₃ | —H | —H | N-piperidine-CH(C₆H₅)₂ | 2HCl | — | C₃₃H₄₀O₂N₂·2HCl | 69.58 7.43 4.92 / 69.35 7.45 4.82 |
| 21 | —H | —Cl | —H | —H | morpholine | HCl | 225–230 | C₁₅H₁₈ONCl·HCl | 60.00 6.38 4.67 / 60.17 6.54 4.62 |

Table 1-continued

| Example No. | $R^a$ | $R^b$ | $R^c$ | $R^d$ | $R^e$ | Salt | Melting point (°C.) (decomposition) | Molecular formula | Elemental analysis (%)* C | H | N |
|---|---|---|---|---|---|---|---|---|---|---|---|
| 22 | —H | —OCH$_3$ | —H | —H | piperazine-N—CH$_2$COOC$_2$H$_5$ | 2HCl | 192–197 | C$_{20}$H$_{28}$O$_3$N$_2$·2HCl·H$_2$O | 55.17 55.44 | 7.41 7.39 | 6.43 6.35 |
| 23 | —O—CH$_2$—O— | | —H | —H | morpholine | HCl | 237 | C$_{16}$H$_{19}$O$_3$N·HCl | 62.03 61.93 | 6.51 6.56 | 4.52 4.41 |
| 24 | —OC$_4$H$_9$ | —OC$_4$H$_9$ | —H | —H | morpholine | HCl | 196–201 | C$_{23}$H$_{35}$O$_3$N·HCl | 67.38 67.35 | 8.85 8.91 | 3.42 3.53 |
| 25 | —H | —H | —H | —H | piperazine-N—CO(CH$_2$)$_2$CH$_3$ | HCl | 198–208 | C$_{19}$H$_{26}$ON$_2$·HCl | 68.14 67.99 | 8.13 8.14 | 8.37 8.44 |
| 26 | —H | —OCH$_3$ | —H | —H | piperazine-N—CH$_2$CON(pyrrolidine) | 2HCl | 210–220 | C$_{22}$H$_{31}$O$_2$N$_3$·2HCl | 59.72 59.43 | 7.52 7.54 | 9.50 9.35 |
| 27 | —H | —H | —H | —H | piperazine-N—CO-(3-pyridyl) | 2HCl | 219–221 | C$_{21}$H$_{23}$ON$_3$·2HCl·½H$_2$O | 60.72 61.12 | 6.31 6.18 | 10.12 10.22 |
| 28 | —H | —H | —H | —H | piperazine-NH | 2HCl | 238–258 | C$_{15}$H$_{20}$N$_2$·2HCl·H$_2$O | 56.42 56.17 | 7.58 7.33 | 8.77 8.95 |
| 29 | —H | —H | —H | —H | piperazine-N—CO-(3,4,5-trimethoxyphenyl) | HCl | 215–225 | C$_{25}$H$_{30}$O$_4$N$_2$·HCl | 65.42 65.17 | 6.81 6.83 | 6.10 5.89 |

*Calculated values in top rows, and found values in bottom rows.

EXAMPLE 30

In 30 ml. of ethanol is dissolved a mixture of 2 g. of 6-methoxy-3,4-dihydro-1(2H)-naphthalenone, 4 g. of 1-benzhydrylpiperazine hydrochloride and 4 g. of 37% aqueous formalin and the solution is allowed to stand at room temperature for 7 days. To the reaction mixture is added 500 ml. of water and, after shaking with 100 ml. of diethyl ether, the water layer is neutralized with sodium hydrogen carbonate and extracted with 200 ml. of cloroform. The extract is dried over anhydrous sodium sulfate and distilled under reduced pressure to remove the solvent. The residue is crystallized by the addition of methanol. By the above procedure is obtained 3.5 g. of 2-(4-benzhydryl-1-piperazinylmethyl)-6-methoxy-3,4-dihydro-1(2H)-naphthalenone as colorless crystals melting at 158°–160° C.

Elemental analysis, for $C_{29}H_{32}O_2N_2$ — Calculated: C, 79.06; H, 7.32; N, 6.36. Found: C, 78.71; H, 7.31; N, 6.21.

In a mixture of 50 ml. of chloroform and 100 ml. of methanol is dissolved 3.5 g. of 2-(4-benzhydryl-1-piperazinylmethyl)-6-methoxy-3,4-dihydro-1(2H)-naphthalenone. Following the addition of 3 g. of sodium borohydride, the solution is stirred at room temperature for 30 minutes. The reaction mixture is then diluted with 500 ml. of water and extracted with chloroform. The extract is dried over anhydrous sodium sulfate and distilled under reduced pressure to remove the solvent, whereby 3 g. of 2-(4-benzhydryl-1-piperazinylmethyl)-6-methoxy-1,2,3,4-tetrahydro-1-naphthalenol is obtained as oily residue. This residue is dissolved in a mixture of 20 ml. of 20% ethanolic hydrochloric acid and 30 ml. of ethanol, and the solution is heated at 80°–90° C. for 30 minutes. The reaction mixture is cooled to obtain 2.7 g. of 3-(4-benzhydryl-1-piperazinylmethyl)-7-methoxy-1,2-dihydronaphthalene hydrochloride as colorless needles melting at 220°–235° C. (gradually decomposed).

Elemental analysis, for $C_{29}H_{32}ON_2 \cdot 2HCl$ — Calculated: C, 70.01; H, 6.89; N, 5.63. Found: C, 69.99; H, 6.92; N, 5.63.

In 50 ml. of methanol is dissolved 1 g. of 3-(4-benzhydryl-1-piperazinylmethyl)-7-methoxy-1,2-dihydronaphthalene hydrochloride with gentle heating, and the solution is neutralized with the addition of an aqueous soluton of sodium hydrogen carbonate under stirring and extracted with chloroform. The extract is dried over anhydrous sodium sulfate and distilled under reduced pressure to remove the solvent. The residue is dissolved in 10 ml. of ethanol. To the resulting solution is added dropwise a solution of 0.4 g. of concentrated sulfuric acid dissolved in 20 ml. of ethanol and then is added gradually 400 ml. of diethyl ether to obtain 1 g. of 3-(4-benzhydryl-1-piperazinylmethyl)-7-methoxy-1,2-dihydronaphthalene dihydrogen sulfate as colorless crystalline powder melting at 150°–165° C. (gradually decomposed).

Elemental analysis, for $C_{29}H_{32}ON_2 \cdot 2H_2SO_4 \cdot H_2O \cdot \frac{1}{2}(C_2H_5)_2O$ Calculated: C, 55.10; H, 6.41; N, 4.15. Found: C, 55.17; H, 6.44; N, 3.98.

EXAMPLES 31 to 39

The 1,2-dihydronaphthalene derivatives listed in Table 2 are produced by subjecting the corresponding tetralol compounds to dehydration reaction in a similar manner to those described in the preceding Examples.

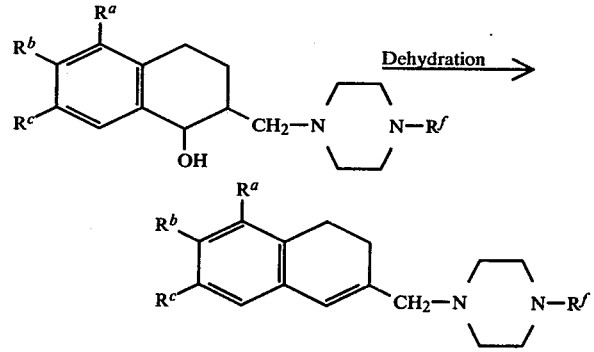

Table 2

| Ex. No. | $R^a$ | $R^b$ | $R^c$ | $R^f$ | Salt | Melting point (° C.) (decomposition) | Molecular formula | Elemental analysis (%)* C | H | N |
|---|---|---|---|---|---|---|---|---|---|---|
| 31 | —H | —OC₄H₉ | —H | —CH(C₆H₅)₂ | 2HCl | 198–205 | $C_{32}H_{38}ON_2 \cdot$ 2HCl | 71.23 70.75 | 7.47 7.40 | 5.19 4.97 |
| 32 | —H | —OC₄H₉ | —H | —CH(C₆H₅)₂ | — | 117–118 | $C_{32}H_{38}ON_2$ | 82.36 82.27 | 8.21 8.21 | 6.00 5.96 |
| 33 | —H | —OC₄H₉ | —H | —CH(C₆H₅)₂ | Maleate | 197–199 | $C_{32}H_{38}ON_2 \cdot$ $C_4H_4O_4$ | 74.19 74.08 | 7.27 7.34 | 4.81 5.09 |
| 34 | —H | —OCH₂—C₆H₅ | —H | —CH(C₆H₅)₂ | 2HCl | 203–208 | $C_{35}H_{36}ON_2 \cdot$ 2HCl | 73.29 73.29 | 6.68 6.64 | 4.88 4.84 |

Table 2-continued

| Ex. No. | $R^a$ | $R^b$ | $R^c$ | $R^f$ | Salt | Melting point (° C.) (decomposition) | Molecular formula | Elemental analysis (%)* C | H | N |
|---|---|---|---|---|---|---|---|---|---|---|
| 35 | —O—CH$_2$—O— | | —H | —CH(C$_6$H$_5$)$_2$ | 2HCl | 235–245 | C$_{29}$H$_{30}$O$_2$N$_2$ . 2HCl | 68.09 68.04 | 6.31 6.17 | 5.48 5.37 |
| 36 | —H | —O—CH$_2$—O— | | —CH(C$_6$H$_5$)$_2$ | 2HCl | 234–245 | C$_{29}$H$_{30}$O$_2$N$_2$ . 2HCl . ½H$_2$O | 66.91 67.00 | 6.39 6.12 | 5.38 5.36 |
| 37 | —H | —OCH$_3$ | —OCH$_3$ | —CH$_2$—C$_6$H$_5$ | 2HCl | 236–240 | C$_{24}$H$_{30}$O$_2$N$_2$ . 2HCl | 63.85 63.85 | 7.15 7.19 | 6.21 6.17 |
| 38 | —OCH$_3$ | —OCH$_3$ | —H | —CH$_2$COOC$_2$H$_5$ | 2HCl | 200–210 | C$_{21}$H$_{30}$O$_2$N$_2$ . 2HCl | 56.37 55.90 | 7.21 7.29 | 6.26 6.51 |
| 39 | —OCH$_3$ | —OCH$_3$ | —H | —CH$_2$—CON< | 2HCl | 230–235 | C$_{23}$H$_{33}$O$_3$N$_3$ . 2HCl . H$_2$O | 56.32 56.33 | 7.60 7.39 | 8.57 8.61 |

*Calculated values in top rows, and found values in bottom rows.

EXAMPLE 40

Where the compound (I) of this invention is administered as a drug for the treatment of impaired cerebral circulation, it may be employed, for example, in accordance with the following formulas.

1. Tablets

| | |
|---|---|
| (1) 3-(4-Benzhydryl-1-piperazinylmethyl)-7,8-dimethoxy-1,2-dihydronaphthalene hydrochloride | 10 mg. |
| (2) Lactose | 90 mg. |
| (3) Starch | 29 mg. |
| (4) Magnesium stearate | 1 mg. |
| | 130 mg. (per tablet) |

(1) and (2) are admixed with 17 mg. of starch and the mixture is granulated with a paste prepared from 7 mg. of starch. To the granules is added 5 mg. of starch and the mixture is compressed into tablets measuring 7 mm. in diameter.

2. Capsules

| | |
|---|---|
| (1) 3-(4-Benzhydryl-1-piperazinylmethyl)-7,8-dimethoxy-1,2-dihydronaphthalene hydrochloride | 10 mg. |
| (2) Lactose | 135 mg. |
| (3) Cellulose powder | 70 mg. |
| (4) Magnesium stearate | 5 mg. |
| | 200 mg. (per capsule) |

All the ingredients are admixed together and packed in gelatin capsules No. 3 (The Pharmacopoeia of Japan, 8th edition).

3. Injections

| | |
|---|---|
| (1) 7,8-Dimethoxy-3-morpholinomethyl-1,2-dihydronaphthalene hydrochloride | 1 mg. |
| (2) Sodium chloride | 9 mg. |
| (3) Chlorobutanol | 5 mg. |
| (4) Sodium hydrogen carbonate | 1 mg. |

All the ingredients are dissolved in 1 ml. of distilled water and filled into brown-colored ampoules, followed by purging with nitrogen gas. The entire process is carried out under sterile conditions.

Experimental

The cerebral blood flow increasing activity of the representatives of the compounds (I):

Dogs weighing 5.5 to 12 kg. were anaesthetized with sodium pentobarbital (30 mg./kg., intravenous injection), and the increase in vertebral blood flow following the administration of the test compounds (1.0 mg./kg., intravenous injection) was determined, with an electromagnetic set around the right vertebral artery. The results are shown in Table 3.

Table 3

| Test compound | No. of experiments | Increase in vertebral blood flow (%)* | | | |
|---|---|---|---|---|---|
| | | 1 min. after dosing | 5 min. after dosing | 10 min. after dosing | 20 min. after dosing |
| 3-(4-Benzhydryl-1-piperazinylmethyl)-7,8-dimethoxy-1,2-dihydronaphthalene hydrochloride | 5 | 56 (±12) | 63 (±23) | 38 (±28) | 31 (±24) |
| 7,8-Dimethoxy-3-morpholinomethyl-1,2-dihydronaphthalene hydrochloride | 5 | 71 (±28) | 14 (±6) | 4 (±2) | — |

*Percent increase = $\dfrac{\text{Blood flow after dosing} - \text{Blood flow before dosing}}{\text{Blood flow before dosing}} \times 100$ The values in parentheses denote standard errors.

What is claimed is:

1. A member of the group consisting of (a) a compound of the formula

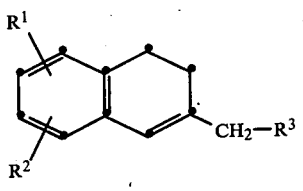

wherein $R^1$ and $R^2$, independently of each other, are hydrogen, nitro, amino, halogen, hydroxyl, lower alkoxy containing up to 5 carbon atoms or aralkyloxy containing a total of 7 to 12 carbon atoms, or $R^1$ and $R^2$ may, taken together, form lower alkylenedioxy containing up to 3 carbon atoms, and $R^3$ is 1-piperazinyl substituted at the $N^4$-position by aralkyl consisting of a straight-chain lower alkyl of 1 to 3 carbon atoms substituted at the ω-position by one or two phenyls, or by carboxylic acid-derived acyl containing a total of up to 10 carbon atoms, and (b) a physiologically acceptable acid addition salt thereof.

2. A compound according to claim 1 wherein aralkyl is benzhydryl.

3. A compound according to claim 1 wherein $R^1$ and $R^2$ are lower alkoxy and $R^3$ is 1-piperazinyl substituted at the $N^4$-position by aralkyl.

4. A compound according to claim 1 wherein $R^1$ is lower alkoxy, $R^2$ is hydrogen and $R^3$ is 1-piperazinyl substituted at the $N^4$-position by aralkyl.

5. A compound according to claim 1, said compound being 3-(4-benzhydryl-1-piperazinylmethyl)-7,8-dimethoxy-1,2-dihydronaphthalene.

6. A compound according to claim 1, said compound being 3-(4-benzhydryl-1-piperazinylmethyl)-1,2-dihydronaphthalene.

7. A compound according to claim 1, said compound being 3-(4-benzhydryl-1-piperazinylmethyl)-6,7-dimethoxy-1,2-dihydronaphthalene.

8. A compound according to claim 1, said compound being 3-(4-benzhydryl-1-piperazinylmethyl)-7-methoxy-1,2-dihydronaphthalene.

9. A compound according to claim 1, said compound being 3-(4-benzhydryl-1-piperazinylmethyl)-7-n-butyloxy-1,2-dihydronaphthalene.

10. A compound according to claim 1, said compound being 3-(4-benzhydryl-1-piperazinylmethyl)-6,7-methylenedioxy-1,2-dihydronaphthalene.

11. A compound according to claim 1, said compound being 3-(4-benzyl-1-piperazinylmethyl)-6,7-dimethoxy-1,2-dihydronaphthalene.

12. A pharmaceutical composition which comprises, as the active ingredient, at least one member of the group consisting of (a) a compound of the formula

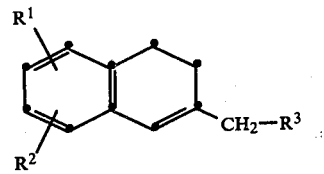

wherein $R^1$ and $R^2$, independently of each other, are hydrogen, nitro, amino, halogen, hydroxyl, lower alkoxy containing up to 5 carbon atoms or aralkyloxy containing a total of 7 to 12 carbon atoms, or $R^1$ and $R^2$ may, taken together, form lower alkylenedioxy containing up to 3 carbon atoms, and $R^3$ is 1-piperazinyl substituted at the $N^4$-position by aralkyl consisting of a straight-chain lower alkyl of 1 to 3 carbon atoms substituted at the ω-position by one or two phenyls, or by carboxylic acid-derived acyl containing a total of up to 10 carbon atoms, and (b) a physiologically acceptable acid addition salt thereof, in admixture with pharmaceutically acceptable carrier, excipient or diluent therefor.

* * * * *